United States Patent [19]
Holcomb

[11] Patent Number: 5,946,102
[45] Date of Patent: Aug. 31, 1999

[54] METHOD AND APPARATUS FOR PARAMETER DIFFERENCE IMAGING OF A SAMPLE SURFACE

[75] Inventor: Matthew J. Holcomb, Manhattan Beach, Calif.

[73] Assignee: MMR Technologies, Inc., Mountain View, Calif.

[21] Appl. No.: 08/900,156

[22] Filed: Jul. 28, 1997

[51] Int. Cl.$^6$ .......................... G01N 21/25; G01N 21/00; G03B 27/42
[52] U.S. Cl. ........................ 356/417; 356/432; 356/73; 356/237; 355/53
[58] Field of Search ................................ 356/417, 432, 356/73, 237; 382/34, 30

[56] References Cited

U.S. PATENT DOCUMENTS

| | | | |
|---|---|---|---|
| 4,653,109 | 3/1987 | Lemelson et al. | 382/34 |
| 5,107,119 | 4/1992 | Kimura et al. | 250/341 |
| 5,175,231 | 12/1992 | Rappoport et al. | 528/106 |
| 5,270,797 | 12/1993 | Pollak | 356/417 |
| 5,439,291 | 8/1995 | Reading | 374/11 |
| 5,490,728 | 2/1996 | Schietinger et al. | 374/7 |
| 5,543,919 | 8/1996 | Mumola | 356/382 |

*Primary Examiner*—Frank G. Font
*Assistant Examiner*—Roy M. Punnoose
*Attorney, Agent, or Firm*—Lumen Intellectual Property Services

[57] ABSTRACT

Physical properties such as composition, purity, or doping level of a sample surface can be measured and imaged using the apparatus and method disclosed herein. Imaging is performed by the following steps:

1) illuminating the sample surface with uniform, monochromatic light and capturing a first image of the reflected light with a CCD camera,
2) uniformly and precisely changing a physical parameter of the sample,
3) repeating step 1 to capture a second image influenced by the new value of the physical parameter,
4) subtracting the first and second images and dividing the result by the average of the images to produce a normalized difference image.

The physical parameter may be temperature, as in the preferred embodiment, electric field, light exposure (at a wavelength different from that used to obtain the image), magnetic field, or mechanical stress. The image produced is of the differential reflectance of the sample surface at a given wavelength. Differential reflectance is equal to the change in reflectance due to the parameter change divided by the average reflectance. The present invention can measure composition, purity, or doping variations over the surface of the sample because these physical properties can affect the differential reflectance. The invention can be used to image the doping type and doping level of semiconductor materials or the composition uniformity of the high $T_c$ superconductors, for example.

12 Claims, 14 Drawing Sheets

METHOD AND APPARATUS FOR PARAMETER DIFFERENCE IMAGING OF A SAMPLE SURFACE

FIELD OF THE INVENTION

This invention relates to measurements of physical properties of materials and thin films, and, more specifically, to imaging physical properties of materials using parameter difference techniques. Thermal Difference, Electro-Difference, Photo-difference, and Magneto-Difference techniques are examples of parameter difference techniques that can be used. The present invention has many applications related to the measurement of physical properties and the spatial variations of the physical properties.

BACKGROUND OF THE INVENTION

The measurement of physical properties of materials is of great importance in many industries. In the semiconductor industry, for example, it is often necessary to know the dopant level and dopant uniformity in a semiconductor wafer. Similarly, it may be useful to be able to measure the uniformity, quality, or purity of thin films of materials such as insulators, metals, or superconductors. For some applications of superconducting thin films, for example, it would be advantageous to be able to check that the superconducting thin film is of uniform quality and composition. Further, it would be advantageous to monitor the growth of such superconducting thin films. These are just a few of the practical applications of material physical property measurement.

U.S. Pat. No. 5,543,919 to Mumola describes an apparatus and method for measuring with high spatial resolution the thickness of a thin film. The apparatus uses a monochromatic light source to illuminate the thin film and a CCD camera to capture an image of the reflected light. Interference fringe patterns are analyzed to obtain a thickness profile of the entire surface imaged. Multiple exposures at different wavelengths may be used to eliminate thickness ambiguities. Mumolas device is not capable of measuring composition uniformity or many other physical properties of the sample material. The method and apparatus can only be used to measure the thickness of a thin film. A notable feature of this invention is that it does not impose a physical parameter change such as a change in temperature on the sample.

U.S. Pat. No. 5,107,119 to Kimura et al. describes a method and apparatus for measuring physical properties of superconducting thin films. The invention works by passing far-infrared light through the thin film and analyzing the spectrum of the light transmitted. Some notable features of Kimuras apparatus are: 1) it measures light transmittance, not reflectance, 2) it is not an imaging technique, 3) it uses a broadband, not monochromatic, infrared source, and 4) it is limited for use with superconducting materials. Kimura's apparatus is not capable of measuring the composition and composition uniformity of a variety of materials.

U.S. Pat. No. 5,490,728 to Scheitinger et al. describes methods for measuring physical properties of a surface with noncontact optical techniques. The surface is illuminated with white light having a temporal intensity ripple. The spectrum and intensity of the light reflected by the surface and the thermal radiation emitted by the surface are measured. Precise determinations of emissivity, reflectivity, temperature, changing surface composition, the existence of any layer formed on the surface and its thickness are all possible from this measurement. Scheitingers invention is particularly applicable to semiconductor wafer processing and metal processing. Scheitinger does not image the surface to provide a spatial map of the characteristics measured. Therefore, the method can be of limited use for some applications. Three important notable features of Scheitingers invention are: 1) it does not compare multiple images of the surface, 2) the incident light is time-varying, and 3) the incident light is broadband, not monochromatic.

U.S. Pat. No. 5,439,291 to Reading describes a technique for determining physical properties of a sample using thermal modulation techniques. Two identical samples are used, with one experiencing a linear temperature ramp and the other experiencing the same ramp with a temperature oscillation imposed. A chopped light source can be used to provide the energy necessary for the temperature oscillation. Thermocouples attached to each sample measure the temperature of each sample, which is the diagnostic means. This invention does not image the samples. Light is only used as a radiation source to heat the temperature-modulated sample, and is not used as a diagnostic means.

The prior art devices do not provide a means for imaging the composition or other physical properties of a sample surface. The dopant level of semiconductor wafers, for example, cannot be imaged using the prior art techniques. Also, the composition and composition uniformity of superconducting thin films cannot be imaged.

Therefore, there exists a need for a technique for imaging physical properties such as composition of a material sample using noncontact techniques. Further, it would be advantageous for this technique to be applicable to many different types of materials.

OBJECTS AND ADVANTAGES OF THE INVENTION

It is an object of the present invention to provide a method and apparatus for imaging and measuring physical properties of a material sample that:

1) can be used to image and measure a variety of physical properties;
2) does not require contact with the sample tested;
3) can be used to test many different types of materials such as semiconductors, metals, superconductors, and insulators;
4) has a relatively high sensitivity to the physical properties measured;
5) is nondestructive to the sample material.

SUMMARY OF THE INVENTION

These objects and advantages are attained by applying a novel technique known as parameter-difference imaging. The parameter may be temperature, electric field, photon exposure, magnetic field, or any other parameter that can be varied to produce a parameter difference spectrum.

If temperature is the varied parameter, the technique is called thermal-difference imaging (TDI), similarly, electric field, photon exposure, and magnetic field versions are called electro-difference imaging (EDI), Photo-difference imaging (PDI), and magneto-difference imaging (MDI), respectively.

The method for TDI begins with uniformly illuminating a sample held at a predetermined, uniform temperature with monochromatic light of a predetermined wavelength. The light reflected from the surface is imaged onto an electronic camera such as a CCD camera and the image is stored. The temperature of the sample is then uniformly changed by a predetermined amount, typically 5–10° C. A second image of the reflected monochromatic light is captured with the sample at the new temperature. All the conditions during the two image acquisitions are identical except the sample temperature (more generally, the difference parameter). Next, the two images are subtracted and the result is divided by the average intensity of the two images to produce a normalized difference image.

In EDI, an electric field is imposed on the sample and varied between the two image acquisitions. For imaging a thin wafer, for example, the electric field is perpendicular to the wafer and is produced by a pair of planar electrodes parallel to the wafer. The top electrode must be transparent to the wavelength of light used, of course.

PDI exposes the sample to a wavelength of light different than the wavelength used for imaging.

MDI uses a magnet (permanent magnet or electromagnet) to vary an imposed magnetic field.

A perfectly uniform sample will produce a uniform difference image when the images are subtracted.

Different regions of a sample with nonuniform composition will have reflectances with different temperature (parameter) dependencies. Therefore, the difference image will not be uniform and will indicate those regions with varied composition.

Numerous physical properties such as composition, phase and crystal orientation can be inferred from the difference image. The physical properties imaged will depend upon the sample material, the wavelength of light used for imaging, and the difference parameter used.

The wavelength of light used to illuminate the sample is selected by analyzing the parameter difference spectrum of the sample material. Preferably, the wavelength used is in a wavelength range where the differential reflectivity (i.e., the parameter difference spectrum curve) has a large derivative with respect to wavelength. Also preferably, the wavelength used is located where the differential reflectance equals zero. For many materials, these two conditions are coincident.

DETAILED DESCRIPTION

In order to understand thermal difference imaging, one must understand the known technique of thermal difference spectroscopy. Reference can be made to "Thermal Difference Spectroscopy", *Rev. Sci. Instruments* 64 (7), July 1993 or "Thermal-Difference Reflectance Spectroscopy of the High-Temperature Cuprate Superconductors", *Physical Review B*, V53 (10) Mar. 1, 1996.

Figure 1:
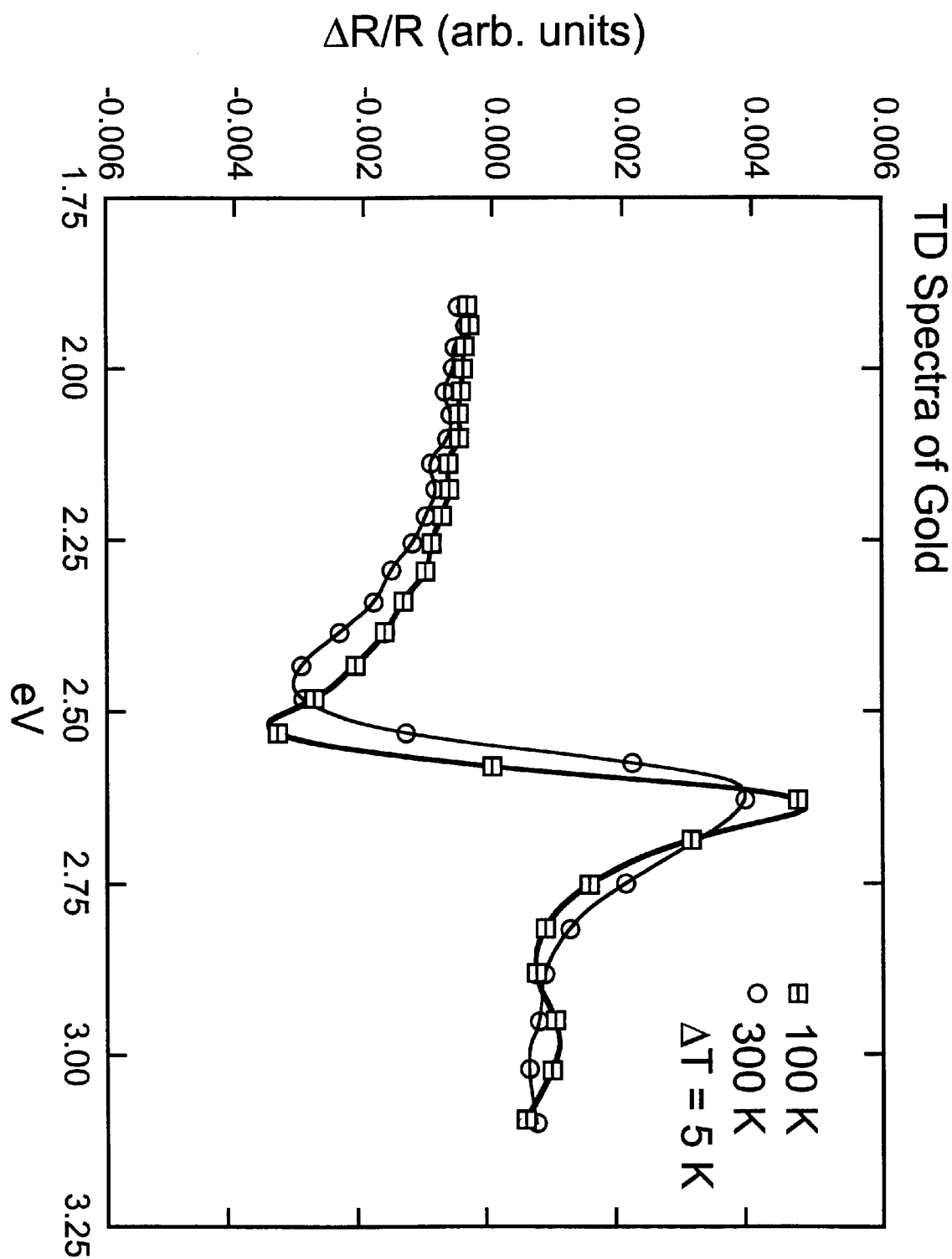
FIG. 1 is a graph of the thermal difference spectrum of gold with T=300K and $\Delta T$=5K taken between 2.0 and 3.0 eV.
Figure 2:
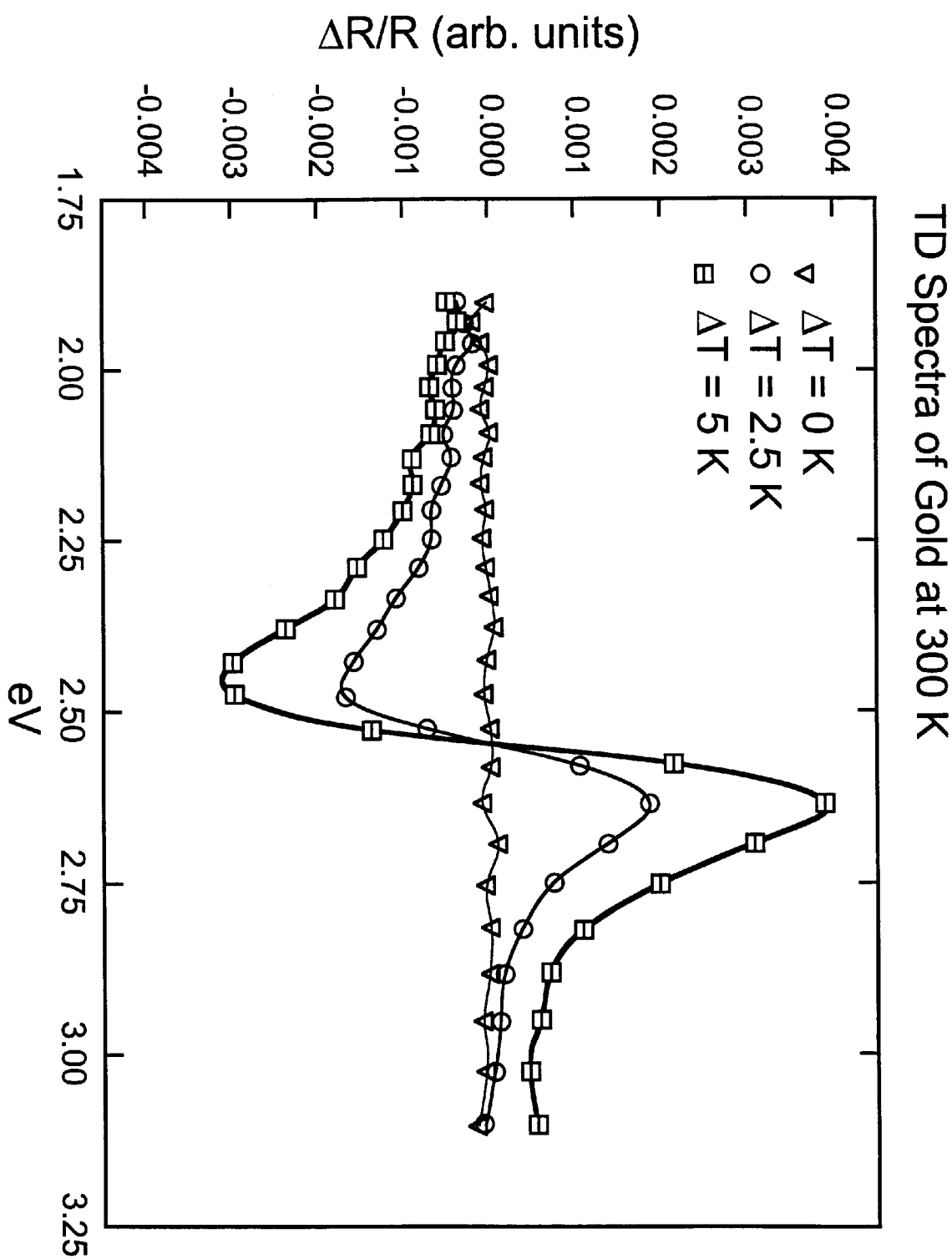
FIG. 2 is a graph of three thermal difference spectra of gold with T=300K and $\Delta T$=0K, 2.5K, and 5K taken between 2.0 and 3.0 eV.

Thermal difference (TD) spectroscopy is performed by measuring the reflectivity of a sample at two different temperatures over a wavelength range of interest. The reflectivity is measured at a single point on the sample surface. FIG. 1 shows two TD spectra of gold from 2.0 to 3.0 eV at 300K and 100K where $\Delta T$=5K, i.e. the reflectance is measured at 295K and 305K and at 95K and 105K. The differential reflectance, $\Delta R/R$, is the reflectance change between the two temperatures divided by the average reflectance (the normalized differential reflectance). Differential reflectance (DR) measurements are made over a range of photon energies. Generally, the absolute value of the DR is proportional to $\Delta T$ for small values of $\Delta T$. FIG. 2 illustrates this relationship in the gold TD spectrum.

Thermal difference spectroscopy is performed on a single spot of a sample and is therefore non-imaging. The spatial variations in the TD spectrum of a nonuniform sample can only be seen by making many TD spectra measurements in different locations. This fact renders TD spectroscopy unpractical to measure variations of a sample surface in an imaging fashion, particularly if high spatial resolution is required.

FIGS. 3A–3D show thermal difference (TD) spectra of several different high critical temperature ceramic superconductors. The spectra are taken at two different temperatures: 300K and 105K, 115K, or 135K. The high derivative response at the DR ($\Delta R/R$) zero crossing is a characteristic of the high $T_c$ superconductors and is important in the proper application of the present invention. High derivative/zero crossing structures are also present in many other materials such as metals, semiconductors and insulators, although it may have different physical origins.

Thermal difference imaging (TDI), a preferred embodiment of the present invention, uses a single photon energy to illuminate the entire sample surface. The method is not spectroscopic in nature because a single photon energy is used. The image produced by TDI indicates the variations in the DR of an entire sample surface at the single photon energy used. Variations in the DR can indicate variations in the composition, doping or other physical properties of the sample. Thus, TDI offers a method for imaging the sample surface, where TD spectroscopy cannot. Further, TDI can produce a high resolution image.

Figure 4:
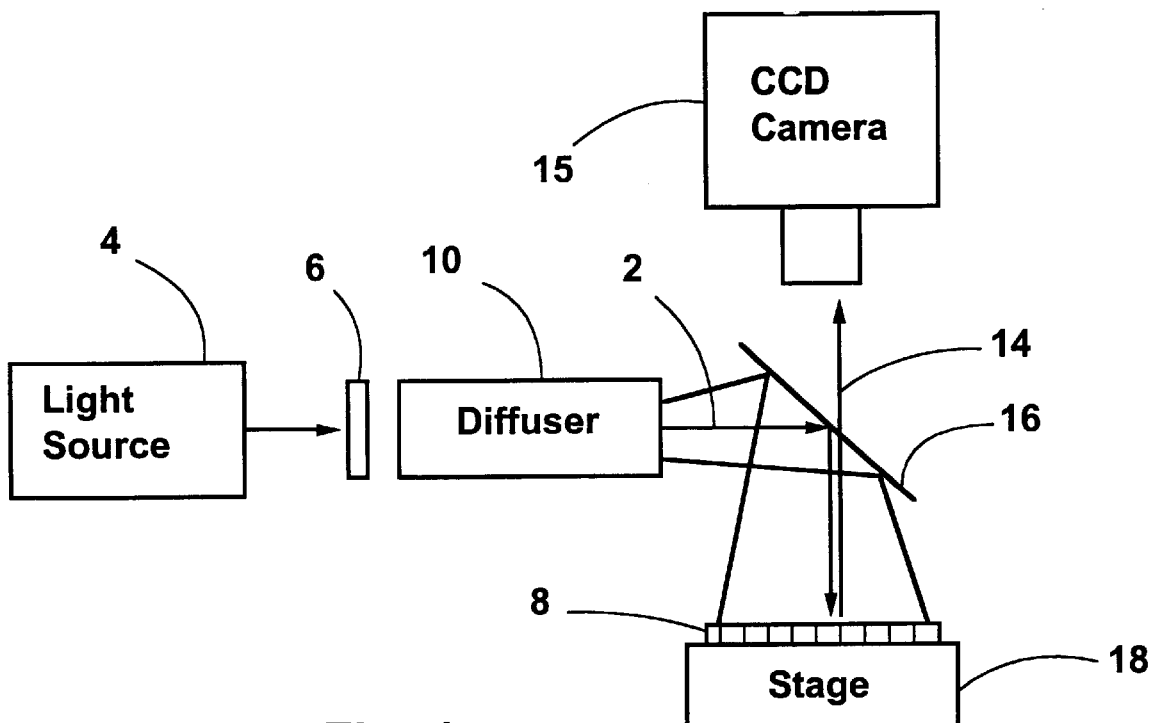
FIG. 4 is a side view of a thermal difference imaging instrument according to the present invention.

FIG. 4 shows a side view of a thermal difference imaging instrument. Monochromatic light 2 from a white light source 4 with a bandpass filter 6 is uniformly projected onto a surface of a sample 8. Preferably, the light passes through a diffuser 10 to produce the uniform beam. Light 14 reflected from the sample 8 surface is imaged in a CCD camera 15. This optical arrangement can be accomplished by using a beam splitter 16 as shown.

The CCD camera 15 is preferably a black-and-white, high spatial resolution, low background noise, and high digital resolution type. A CCD camera adequate for use in the TDI instrument is the EDC-1000L available from Electrim Corporation. This camera is a 753×484 CCD array with low background noise and 16 bit digital resolution. Many other cameras are also available from other manufacturers. The resolution and noise requirements of the specific TDI instrument will determine the camera choice and will be obvious to one skilled in the art.

The sample 8 to be imaged is mounted on a variable-temperature stage 18. The design of this stage 18 will be specific to the types of samples 8 to be imaged. The sample stage 18 is designed to maintain a uniform temperature over the surface of the sample 8, and to produce the rapid and precise temperature changes required of the technique. The temperature of the stage may be controlled with a variety of readily available temperature controllers, such as the K-20 programmable temperature controller manufactured by MMR Technologies, Inc. of Mountain View, Calif.

Thermal difference imaging is performed by the following steps:

1) holding the sample at a first uniform temperature, T1;
2) illuminating the sample surface with uniform, monochromatic light of a predetermined photon energy and capturing an image of the reflected light with the CCD camera;
3) bringing the sample to a new uniform temperature, T2, and allowing the temperature to stabilize;
4) illuminating the sample surface with uniform, monochromatic light of the same predetermined photon energy and capturing a second image of the reflected light with the CCD camera;
5) subtracting the first and second images to obtain a difference image; and
6) dividing the difference image by the average of the two images to produce a normalized difference image.

The subtracting step (step 5) and the normalization step (step 6) can be performed by a computer in communication with the CCD camera 15. Based on the teaching of the present specification, it will be obvious to one skilled in the art how to compute a normalized difference image with the use of a computer.

The normalization step is performed on a pixel-by-pixel basis. In other words, each pixel in the difference image is divided by the average of the two original pixels from which the difference image is calculated. If P1 and P2 are the values of individual, corresponding pixels in the first and second images, then the corresponding pixel in the normalized difference image can be calculated according to the following equation:

$$\frac{P1 - P2}{1/2(P1 + P2)}$$

It is noted that the normalization step is not absolutely necessary to obtain useful information about the sample surface. Normalization is advantageous, however, because it removes the baseline and systematic noise from the image.

This method produces a thermal difference image of the sample 8 surface.

With thermal difference techniques, the stated acquisition temperature is the temperature midway between the two temperatures used. The ΔT stated is ½ the temperature difference between the two temperatures used (T1 and T2). For example, a TD image taken at 300K with ΔT=5K takes images at 295K and 305K.

Typically, the ΔT used to collect the TD spectrum of a material is 5K. Since the TD imaging technique is equivalent to measuring the TD reflectance of a material at one wavelength over the entire surface, 5K is also an acceptable ΔT for use in TDI. TD spectroscopy is a technique known in the art, so it will be obvious to those skilled in TDS what the optimum ΔT is for TD imaging.

The photon energy of the monochromatic light 2 used to illuminate the sample is determined by analyzing the TD spectrum of the sample 8. The spectra of FIGS. 3A–3D illustrate features common to many TD spectra that can be used to select a useful photon energy. The photon energy used is located where the TD spectrum curve has a high derivative and preferably where DR=0. The high derivative response means that the optical properties of the sample are relatively sensitive to changes in the physical properties of the material (composition) and the difference parameter. Thus the imaging technique is inherently more sensitive at these photon energies. The magnitude of the DR change will be proportional to the derivative of the TD spectrum at the photon energy used. The DR=0 choice is preferred (but not absolutely necessary) because a perfectly uniform, ideal sample will give a null result in this case, a convenient feature. The bandwidth of the monochromatic light used should be narrow compared to the width of the high derivative structure.

The shape of the high derivative structure is influenced somewhat by the temperature T at which the spectra is taken. Lower temperatures will result in slightly sharper (higher derivative) features. The acquisition temperatures (T1, T2) can be selected such that they straddle critical temperatures such as superconducting critical temperatures or ferromagnetic critical temperatures. This technique is useful if the optical properties of the sample are influenced by the associated critical transition.

Figure 5:
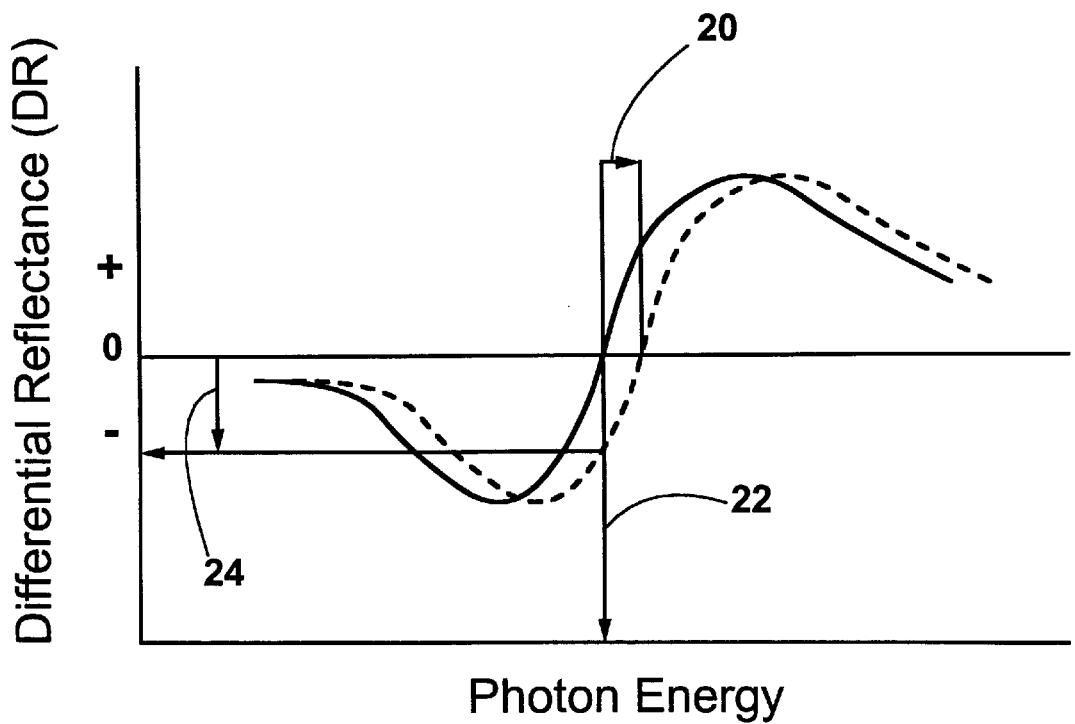
FIG. 5 illustrates how small translations in the TD spectrum of a material can be detected with the present invention.

FIG. 5 illustrates the mechanism by which changes in the TD spectrum are detected with the TDI technique. Small changes in material composition can cause a "horizontal" translation 20 of the materials TD spectrum, or a change in the shape of the TD spectrum curve. In either case, if the photon energy 22 is selected judiciously (i.e., at a high derivative/zero crossing point) the DR at the photon energy used will change by a relatively large amount 24. The value of DR at the photon energy used 22 will thus depend upon the sample composition, which can vary over the sample surface. Upon subtraction and normalization of the images, the change in DR 24 over the sample surface will be imaged, indicating regions of varied composition.

In the parameter difference imaging technique, it is important to keep track of positive and negative values in the difference image. It is the positive and negative values that allow one to determine in which direction (higher or lower photon energy) the TD spectrum of the sample is displaced. Before reliable information about the sample can be obtained, the dependence of the TD spectrum on the composition must be known. This can be accomplished by calibrating the instrument with samples of known composition.

The parameter difference imaging technique measures variations in the DR over the entire surface of the sample. Regions that have different DRs can be assigned a false color. In this way a map can be made of the DR of the surface.

These guidelines also apply to Electro-Difference Imaging (EDI), which uses a variation of an imposed electric field instead of temperature; Photo-Difference Imaging (PDI) which uses a variation of light exposure at a second photon energy, and Magneto-Difference Imaging (MDI), which uses a variation of an imposed magnetic field. These parameter difference imaging techniques are other embodiments of the present invention. In these cases, the Electroreflectance Spectrum (ERS), Photoreflectance Spectrum (PRS) or Magnetoreflectance Spectrum (MRS) would be analyzed to select an appropriate photon energy for imaging. ER spectroscopy, PR spectroscopy and MR spectroscopy are well known in the art. Most generally, the photon energy for Parameter-Difference Imaging (PDI) is selected to be in a high derivative/zero crossing region of the associated parameter reflectance spectrum for any difference parameter (temperature, electric field, photon exposure, magnetic field) used. For all types of parameter reflectance spectroscopy, high derivative regions will generally be located around zero crossings of the differential reflectance.

The ER, PR and MR spectra generally look similar to the TD spectrum of a given material. This is because changes in temperature, electric field, and magnetic field all have similar effects on a materials plasma frequency or electronic transition energies. ER spectra, PR spectra, and MR spectra tend to have sharper peaks, however.

Figure 6:
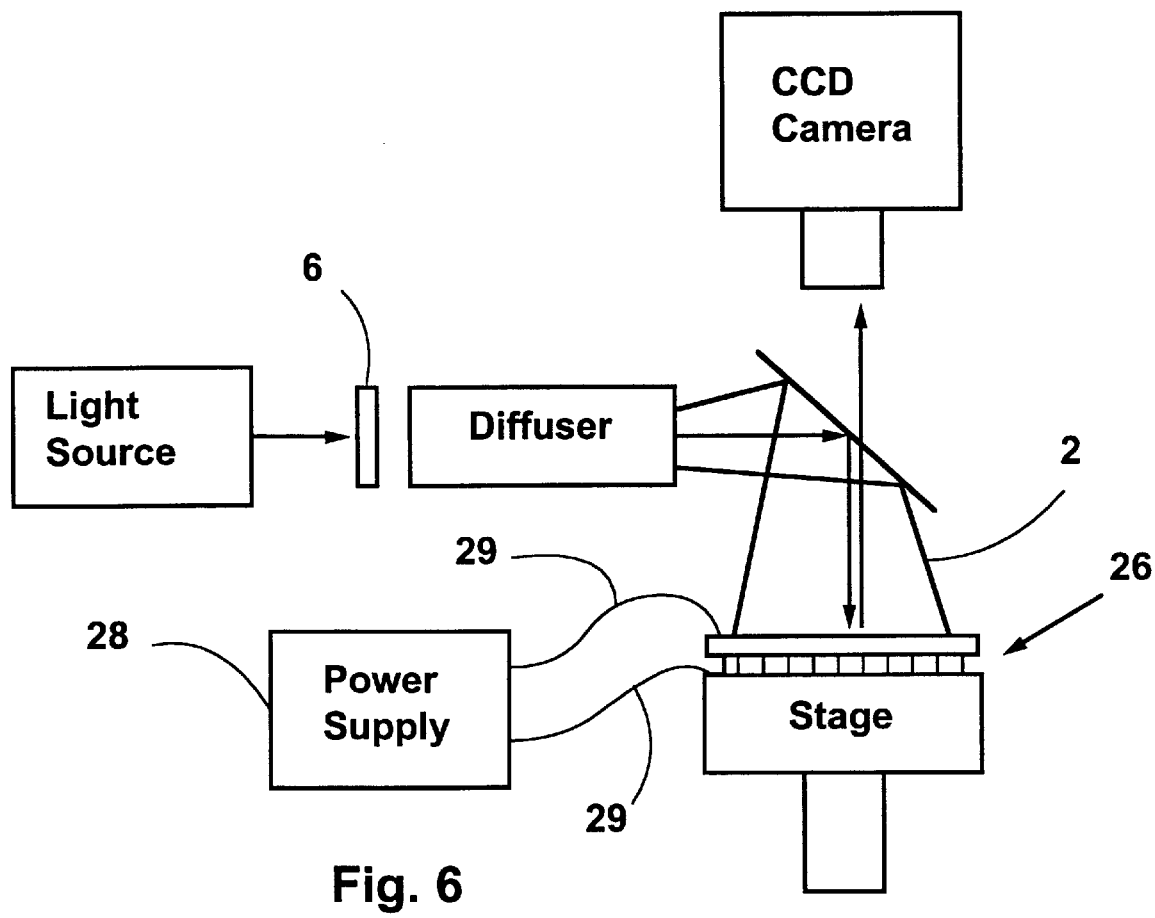
FIG. 6 is a side view of an electro-difference imaging instrument according to the present invention.
Figure 7:
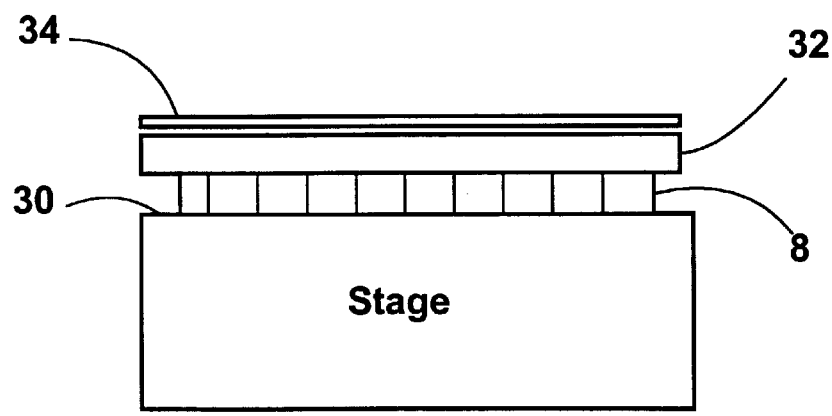
FIG. 7 is a side view of the electric field stage used in the EDI instrument.

FIG. 6 shows an Electro-Difference Imaging instrument according to the present invention. All the elements of the EDI instrument are the same as the TDI instrument except that the variable temperature stage is replaced with a variable electric field stage 26. FIG. 7 shows a closeup of the stage 26, which is designed for flat, thin samples 8. In principle, the samples can be any shape, provided that a uniform electric field can be imposed. Both the polarity and orientation of the electric field with respect to the sample surface or light source is immaterial. However, since the electric field must be uniform over the sample surface, it is simplest to orient the field perpendicular to the sample surface. It is noted that EDI cannot be used on metals or other highly conductive materials that substantially exclude the penetration of an electric field. The electric field sample stage of FIG. 7 comprises a power supply 28, which provides electricity through wires 29, a conductive backing plate 30, the sample 8, and a glass plate 32 with a transparent, conductive film such as an indium tin oxide film 34. The conductive film 34 acts as an electrode while also being transparent to the monochromatic light 2 used for the imaging process. The electric field is developed between the conductive film 34 and the conductive backing plate 30. The magnitude of the electric field is selected in dependence on the sample material and the magnitude of the composition nonuniformities of the sample material. Typical voltages may be 500V for a thin sample. Generally, the electric field magnitude is determined empirically. It will be obvious to one skilled in the art of Electroreflectance Spectroscopy how to analyze the ER spectrum of a material to select an appropriate electric field magnitude in accordance with the present teaching.

The operation of the EDI instrument is analogous to the operation of the TDI instrument. First, a reflectance image of the sample is captured at a low or no electric field, and then a second reflectance image is captured at an elevated electric field. It is also possible to capture two images with applied electric fields of opposite polarities. The two images are subtracted and the result divided by the average of the two images to produce a normalized difference image.

Figure 8:
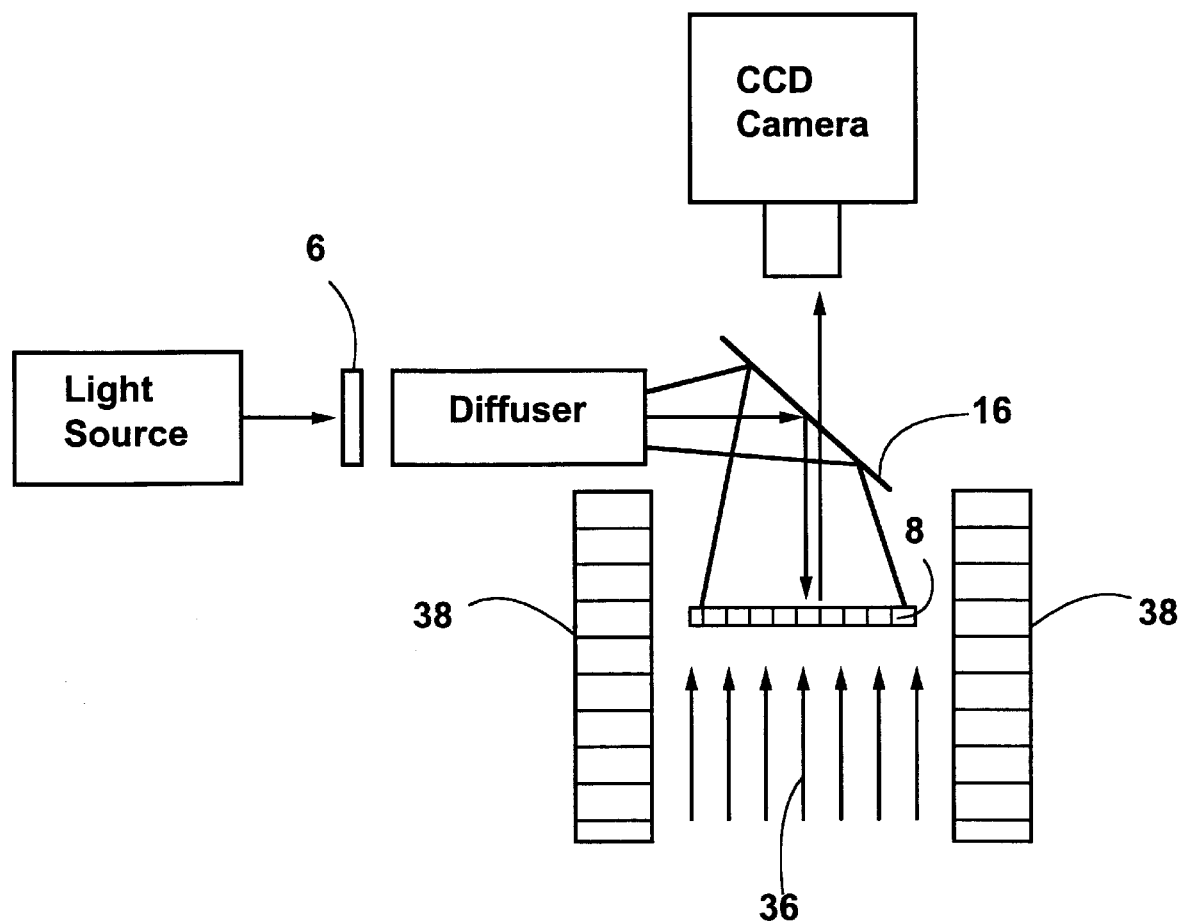
FIG. 8 is a side view of a magneto-difference imaging instrument according to the present invention.

MDI operates analogously to TDI and EDI, using a varied magnetic field 36. FIG. 8 shows an MDI instrument. A solenoid electromagnet 38 can be used to vary the magnetic field 36 in MDI. Permanent magnets can also be used. The imposed magnetic field 36 must be uniform in magnitude and direction. In MDI, the orientation of the magnetic field 36 with respect to the sample 8 may be an important consideration in the case of an anisotropic sample material. It will be obvious to one skilled in the art how to construct an electromagnet 38 with the desired characteristics. The selection of the magnetic field magnitude and direction can be made empirically, but generally fields of a few kilogauss are required.

Figure 9:
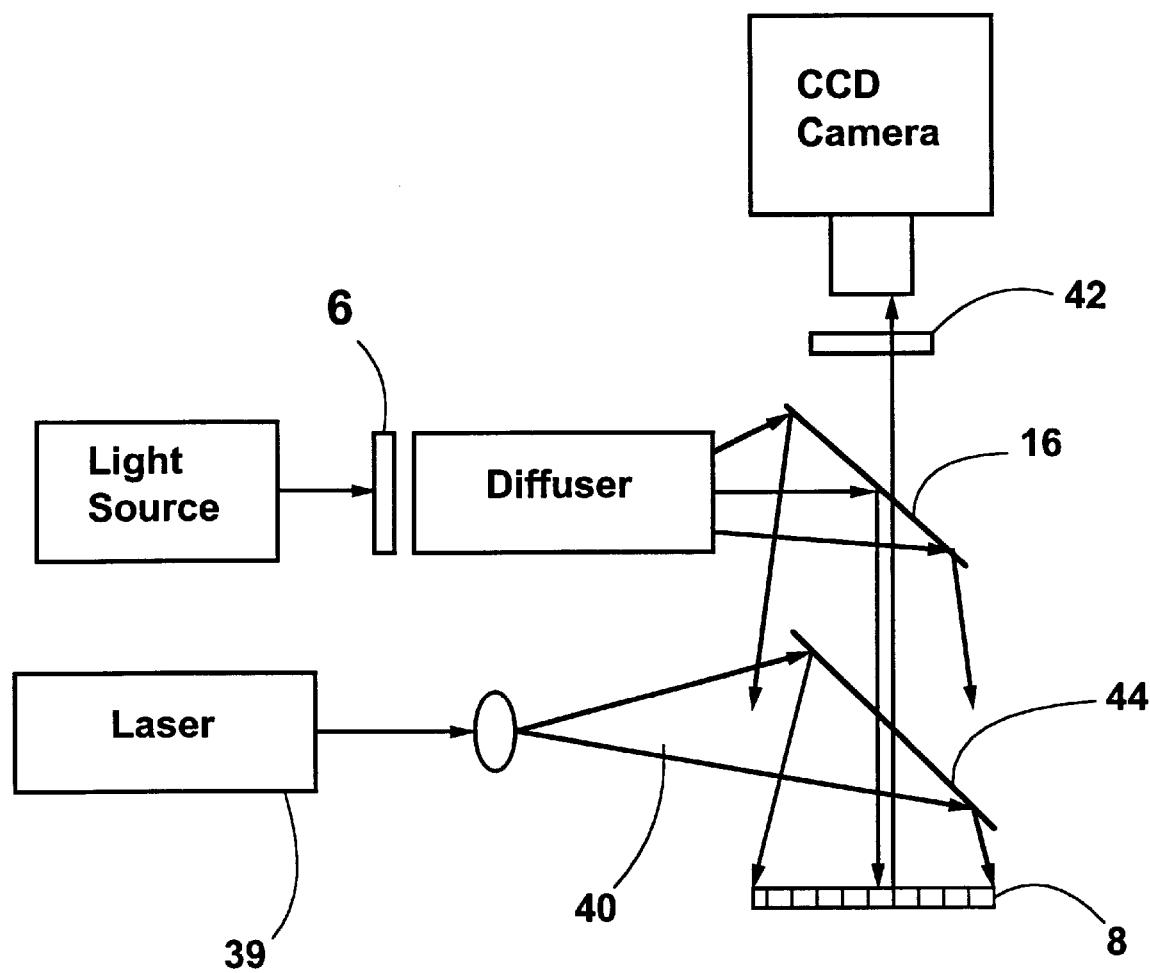
FIG. 9 is a side view of a photo-difference imaging instrument according to the present invention.

PR spectroscopy produces spectra similar to Electro-Difference spectroscopy. In PDI, the parameter varied is the exposure of the sample to monochromatic light of a photon energy different from the light used to measure the reflectance. For example, a PD image can be produced by obtaining a first reflectance image at a wavelength of 400 nm, obtaining a second reflectance image at 400 nm with simultaneous exposure to light at a wavelength other than 400 nm, and then subtracting and normalizing the first and second images. Photo-difference spectroscopy produces the same data as ED spectroscopy because the difference parameter light produces an electric field in the sample. FIG. 9 shows a PD instrument. The parameter difference light 40 can be produced by a laser or other intense light source 39. The parameter difference light 40 must illuminate the sample 8 uniformly. A second beam splitter 44 can be used to project the parameter difference light 40 onto the sample 8. Between the sample 8 and CCD camera 15 is a filter 42 that blocks the parameter difference light 40 and transmits the imaging wavelength 2 (400 nm in the above example). It will be obvious to one skilled in the art Photo-reflectance Spectroscopy how to construct and use Photo-difference imaging instrument in accordance with the present teaching.

It is noted that Piezo-Difference imaging is also possible, and can be analogously adapted from Piezo-Reflectance spectroscopy which is well known in the art. This spectroscopy technique uses a piezo-stage to induce stress in the sample which is bonded to the stage. Stress is the varied parameter. Piezo-Reflectance spectroscopy produces spectra which are similar to TD spectra. It will be obvious to one skilled in the art of Piezorelfectance Spectroscopy how to construct and use a Piezo-Difference imaging instrument in accordance with the present invention.

The high derivative/zero crossing structures that are so important for the present invention are related to the plasma energy (same as plasma frequency) and/or electronic transition energies of a material. The plasma energy and/or transition energies can in turn be related to material composition, doping, or other properties. These facts are used to interpret the parameter difference spectra and can similarly be used to interpret the parameter difference images of a sample surface.

Figure 10:
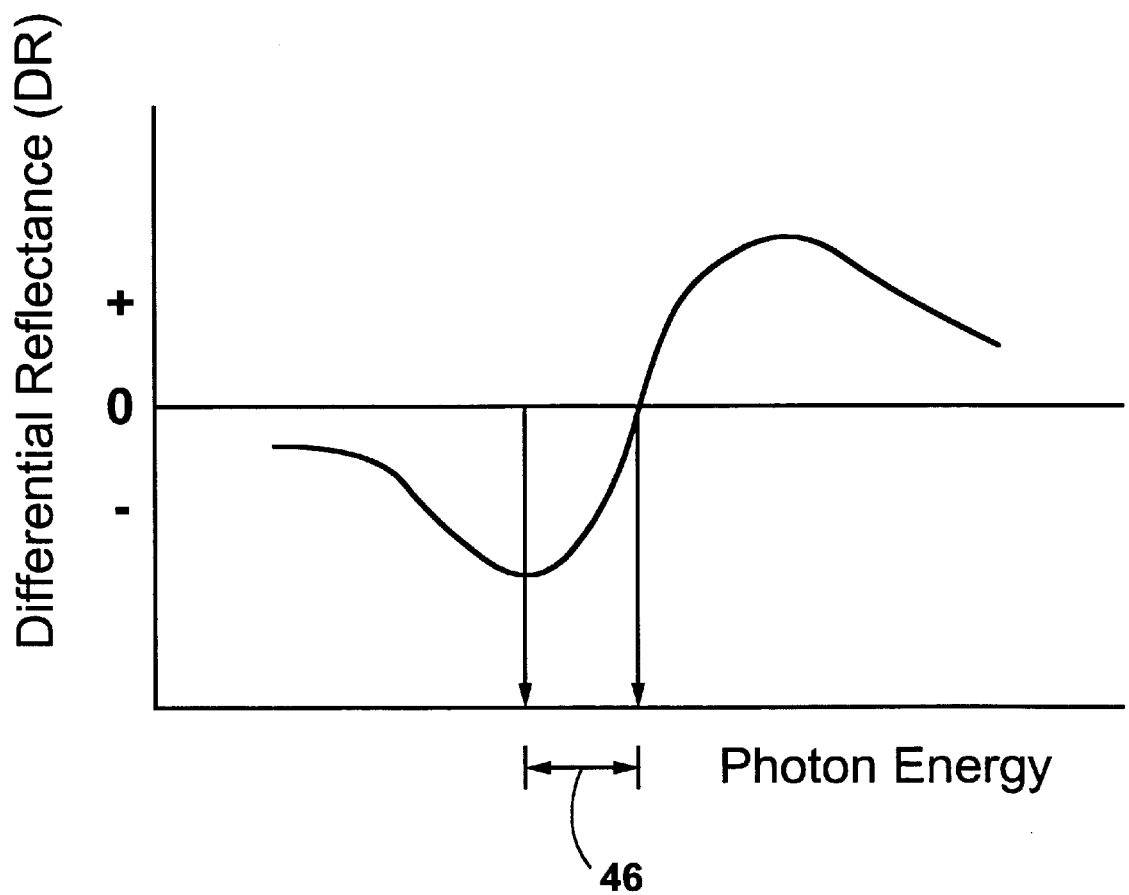
FIG. 10 is a graph of the thermal difference spectrum of a hypothetical conductive material illustrating the effect of the plasma energy upon the TD spectrum.

FIG. 10 shows a TD spectrum of a hypothetical conductive material. The high derivative/zero crossing structure in the TD spectra of conductive materials is caused by the influence of the material's plasma energy. The plasma energy, $\omega p$, is located somewhere in the energy range marked 46, i.e. between the minimum value of DR and the DR zero crossing. The important point here is that if the plasma energy changes, the high derivative structure will move with it. It is well known that the plasma energy in conductive materials is proportional to the square root of the electron density in the material. Thus, a measure of a materials plasma energy gives a measure of the electron density of the material, which can often be related to the doping level or purity. If two regions of a sample surface have different electron densities, they will have different plasma energies and consequently the TD spectra for the two regions will be translated with respect to one another. This is illustrated in FIG. 5. In this situation, it can be seen that two regions with different plasma energies will have different values of DR at the same photon energy. In this way the parameter difference image can be used to image the purity of the material at the sample surface.

Figure 3A:
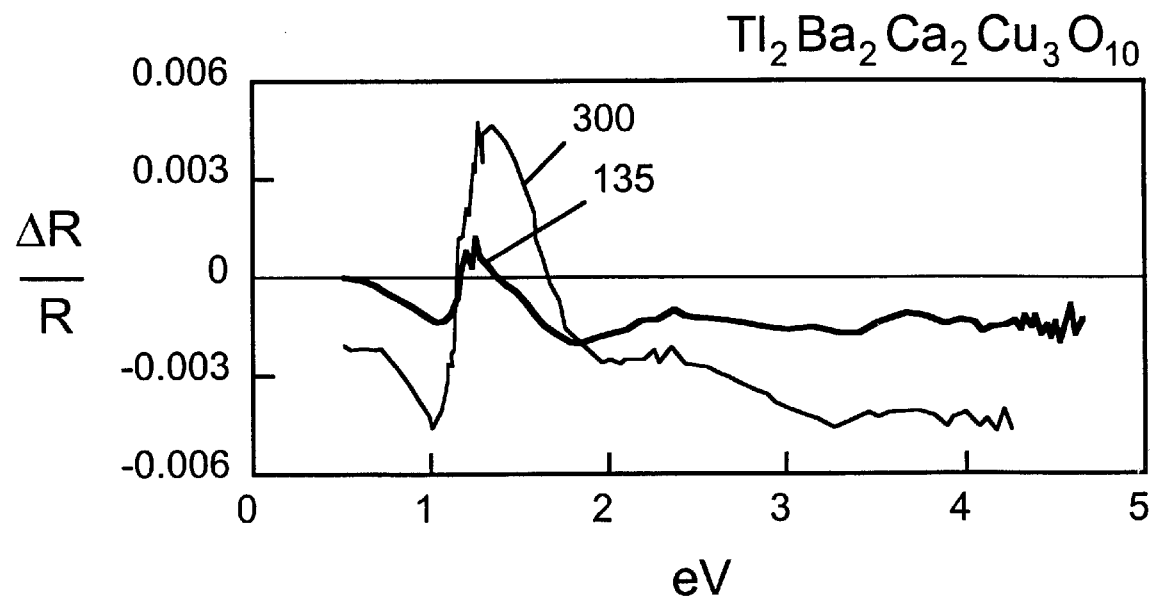
FIGS. 3A–3D are the thermal difference spectra of several different high $T_c$ superconducting materials.
Figure 3B:
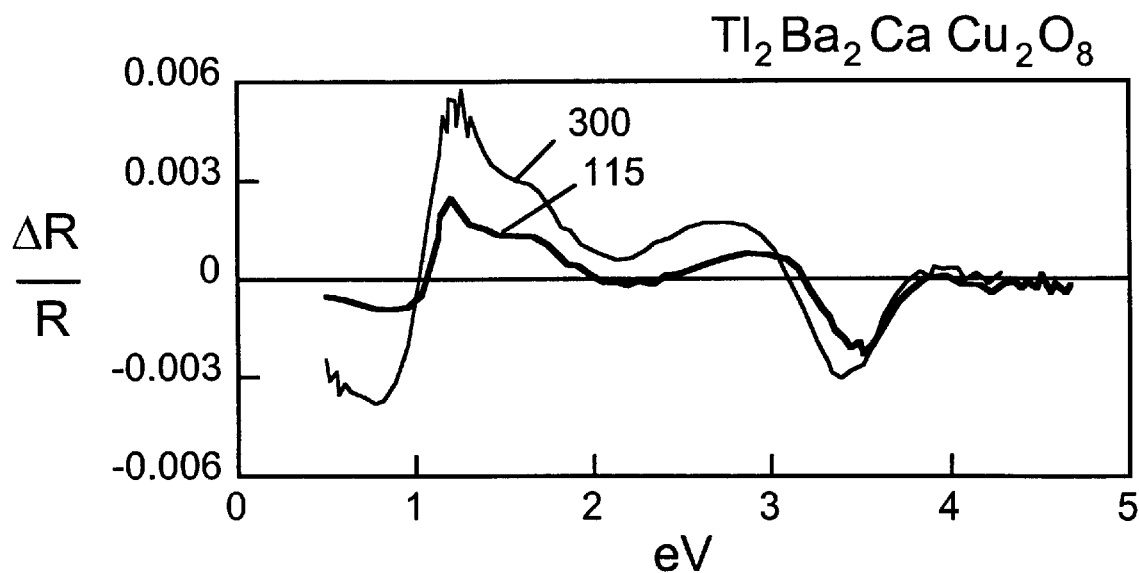
Figure 3C:
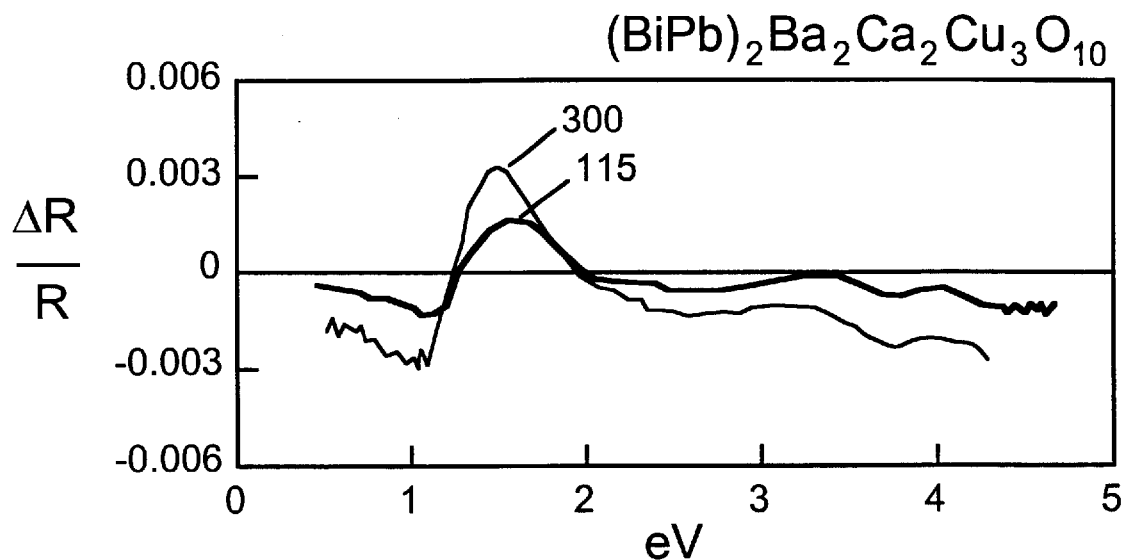
Figure 3D:
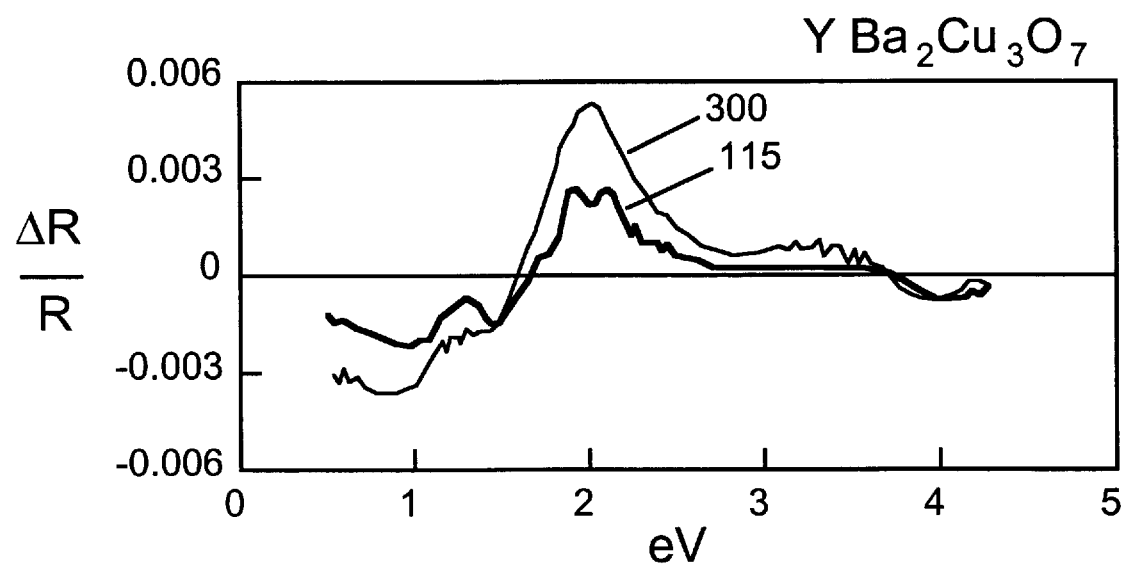

A specific illustrative application of TDI is the imaging of the doping level of oxygen in $Tl_2Ba_2Ca_2Cu_3O_{10}$, a high $T_c$ superconducting material. The room temperature (300K) TD spectrum for this material is shown in FIG. 3A. A large derivative response is located between 1.0 eV and 1.5 eV and is due to the location of the plasma energy. The location of the zero crossing at 1.17 eV is quite sensitive to the doping level of the material, which is also an indication of the $T_c$ of the high $T_c$ superconductors. For $Tl_2Ba_2Ca_2Cu_3O_{10}$, the photon energy used for TDI would be 1.17 eV. Thus, the TD image for an optimum, uniform film of $Tl_2Ba_2Ca_2Cu_3O_{10}$ would result in zero TD signal, a false color we assign to black. Any deviation from optimum doping in the sample would result in a false color differing from black in the TD image. This technique can be extended to many other high $T_c$ materials such as the materials of FIGS. 3B–3D.

TD, ER, PR, and MR spectra are also affected by discrete electronic energy transitions such as band gap transitions. Generally speaking, transitions will result in high derivative/zero crossing structures similar to those associated with the plasma energy. The energies of these transitions dictate the location of the associated high derivative/zero crossing structures. The energies of the electronic transitions are dependent upon sample composition and therefore will change if the sample composition varies. The relationship between the transition energy and the shape of the high derivative/zero crossing structure is typically complicated and cannot be understood as readily as the effect of the plasma energy. The structures associated with electronic transitions are often more complicated and difficult to interpret and therefore the parameter difference image should be empirically calibrated with known samples. With a comparison to known characteristics, useful information can be obtained. Electronic transitions provide the necessary high derivative/zero crossing structures.

Insulators do not have a plasma energy that can be relied upon to provide the necessary high derivative structures in the parameter difference (or reflectance) spectrum. Therefore, performing parameter difference imaging of an insulator requires that electronic transitions be used as a source of structure in the associated parameter difference (or reflectance) spectrum. These transitions result in high derivative/zero crossing structures in most of the parameter difference techniques described.

Figure 12A:
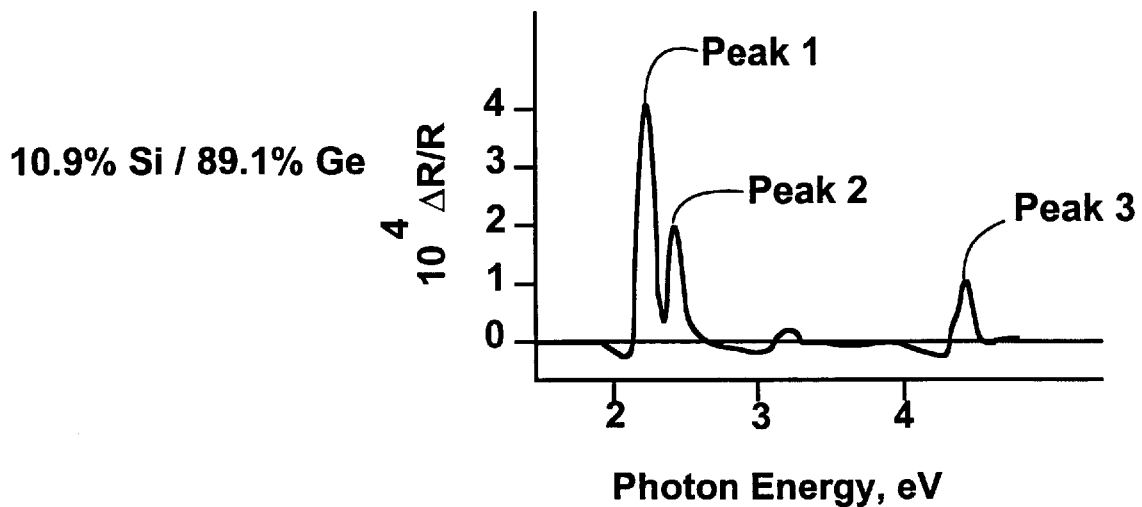
FIG. 12 is a set of graphs of the electroreflectance spectra of two Si—Ge alloys with different compositions.
Figure 12B:
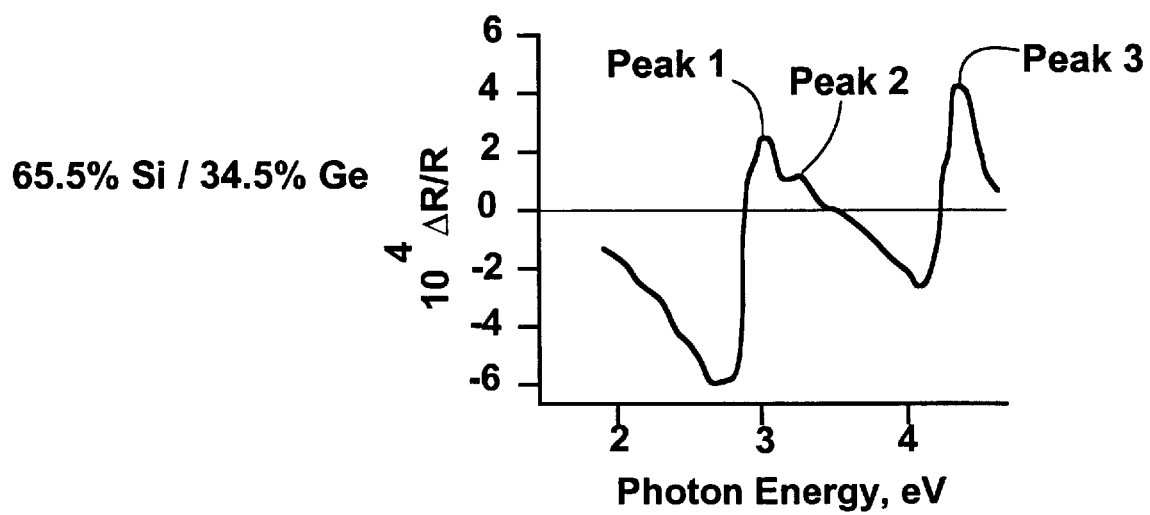
Figure 13:
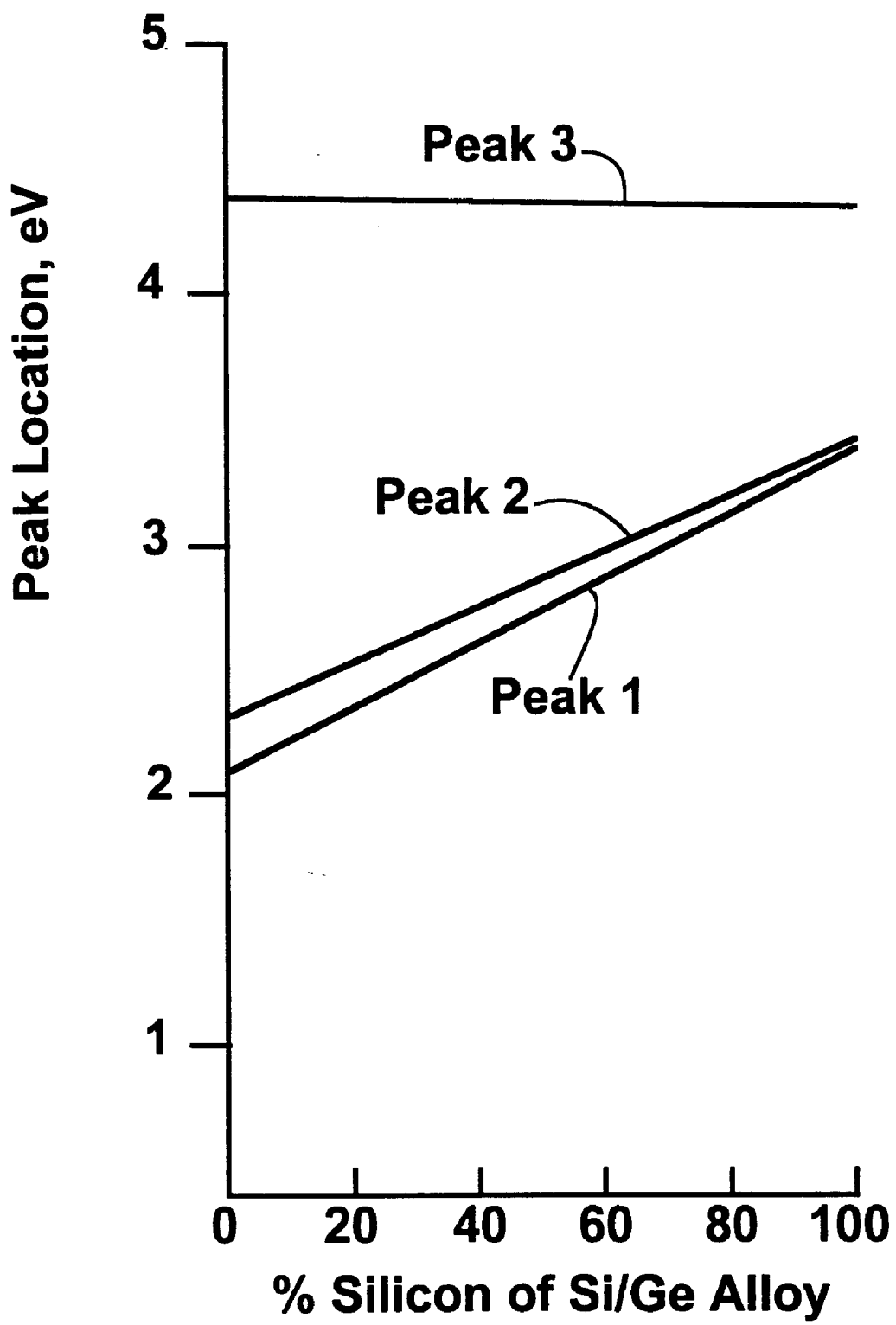
FIG. 13 is a graph illustrating the dependence of the Si—Ge system ER spectrum features upon composition.
Figure 14A:
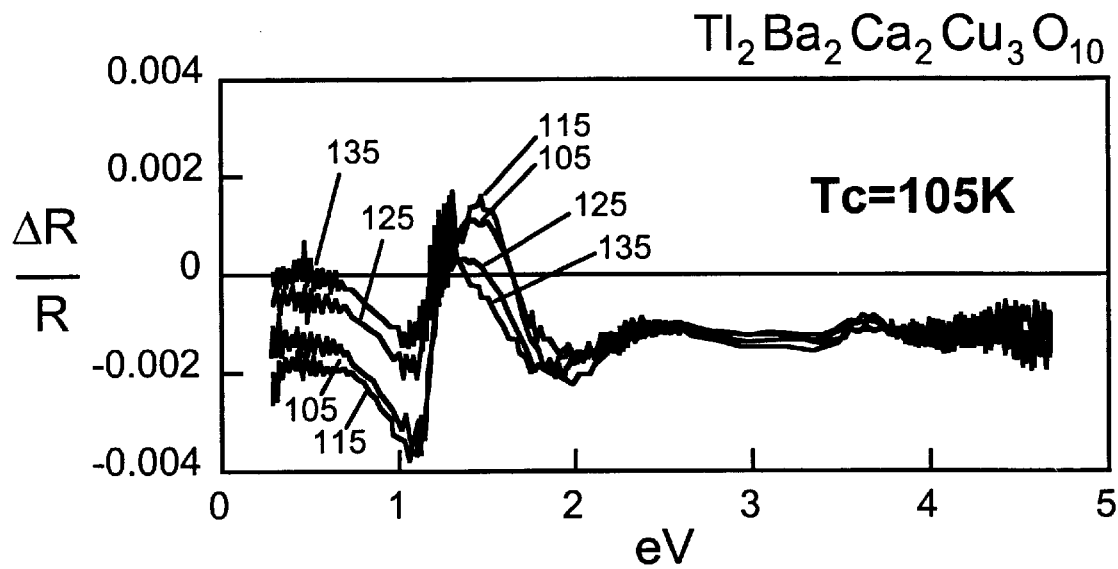
FIGS. 14A–14D are TD spectra of different high $T_c$ superconductors at different temperatures. These spectra illustrate the effect of the superconducting transition on the TD spectra.
Figure 14B:
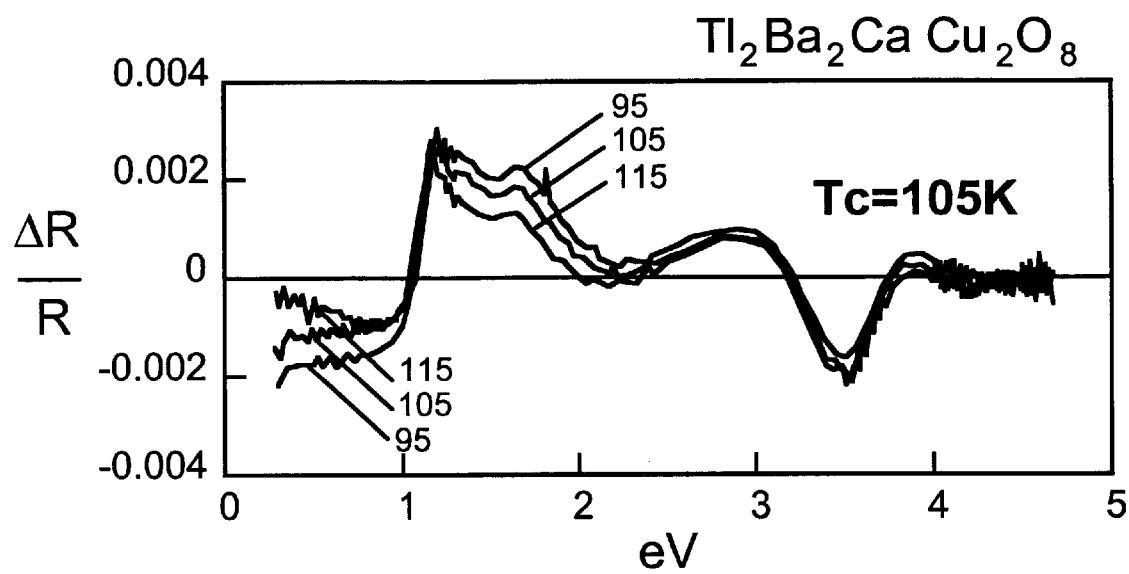
Figure 14C:
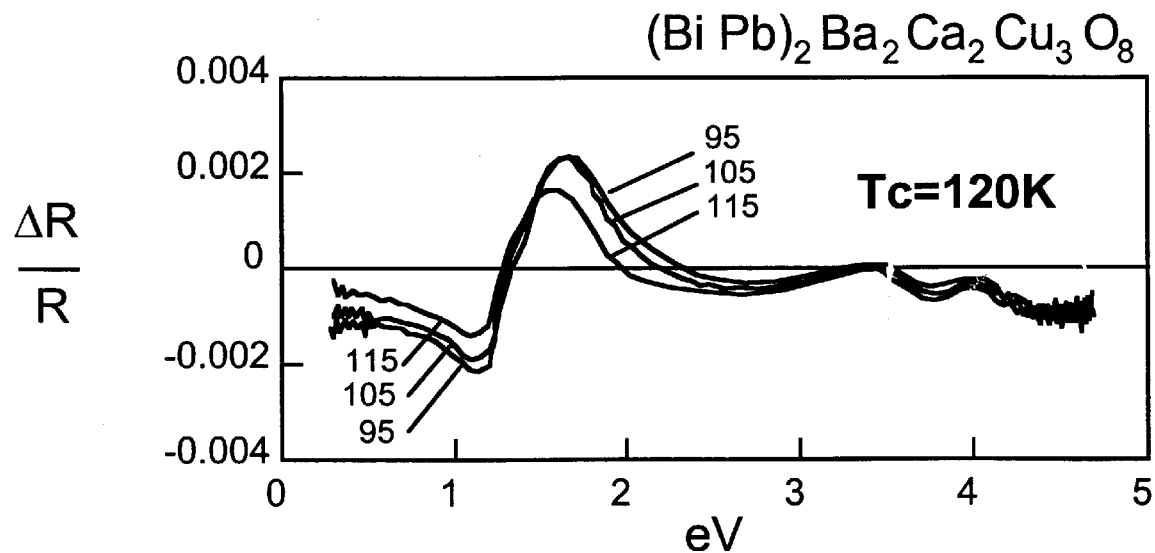
Figure 14D:
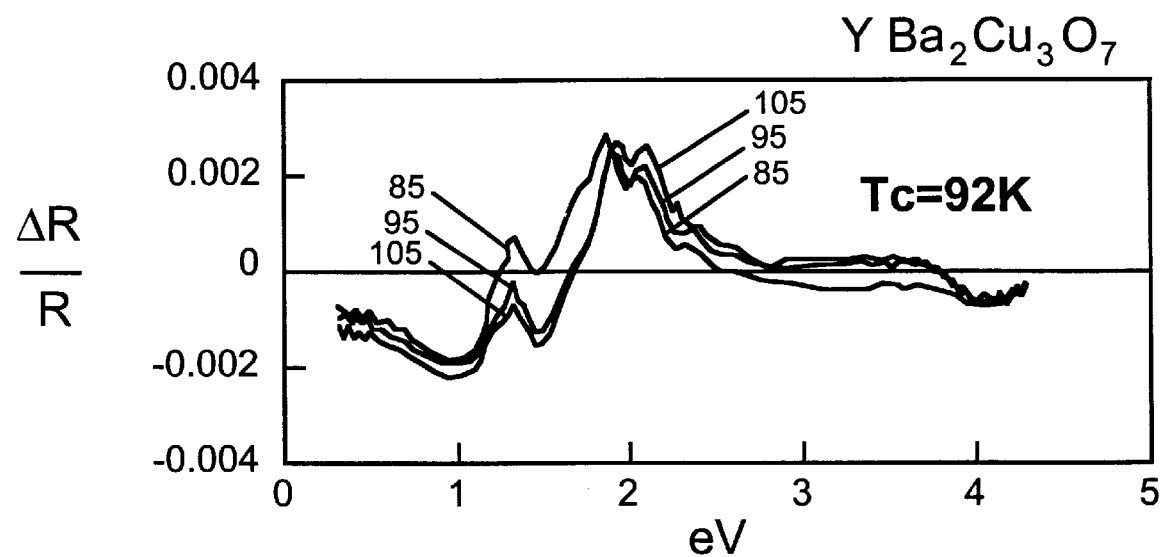

The parameter difference imaging of semiconductors is similar to the imaging of insulators It is well known that the energy of the band gap and certain other transitions in semiconductors is dependent on the doping level. The band gap energy, in turn, affects the energy at which the associated high derivative structure is located. FIG. 11 shows the TD spectra of pure silicon and doped silicon. It can be seen that doping can have a large effect upon the DR value at the photon energies of high derivative/zero crossings. Similar effects are observed with ER spectroscopy and PR spectroscopy. FIG. 12 shows the ER spectra for two Ge—Si alloys. The peaks (Peaks 1,2 and 3) of the graph change in energy according to the graph of FIG. 13 from which it can be seen that the structures (peaks 1, 2, and 3) in the ER spectra move in energy as the composition is varied. It will be obvious to one skilled in the art how these changes in the parameter difference (or reflectance) spectra can be exploited in accordance with the teaching of the present invention to yield images of the doping or composition of a sample surface. Most highly conductive materials such as gold have plasma energies that are far above the visible photon range and outside the range (250–1100 nm) where most standard (silicon) CCD equipment is sensitive. Therefore, for these materials, the high derivative/zero crossing structures associated with electronic transitions must be used. For example, known interband transitions in gold and silver can be used to obtain a TD image of these materials. FIG. 1 shows a high derivative/zero crossing structure in the TD spectrum of gold associated with a d band to Fermi level transition at 300K.

It is known that the optical properties of the high $T_c$ superconductors change slightly upon entry into a superconducting state. The TD spectrum of these materials undergo changes near $T_c$ in the visible region of the spectrum. This is shown in FIGS. 14A–14D. This phenomenon will allow for the non-contact detection of superconductivity over the surface of the sample when the TD image is collected at photon energies where the TD spectrum changes with the onset of superconductivity. Generally, these photon energies are not located where DR=0 The effect can be observed by selecting T and ΔT such that the sample is cycled in and out of the superconducting state. High $T_c$ superconducting materials in which the superconducting state can be imaged include but are not limited to $Tl_2Ba_2Ca_2Cu_3O_{10}$, $YBa_2Cu_3O_7$, $Bi_2Sr_2CaCu_2O_8$, $(BiPb)_2Sr_2Ca_2Cu_3O_{10}$, $Tl_2Ba_2CaCu_2O_8$, and $HgBa_2CaCu_2O_6$.

It will be clear to one skilled in the art that the above embodiment may be altered in many ways without departing from the scope of the invention. Accordingly, the scope of the invention should be determined by the following claims and their legal equivalents.

What is claimed is:

1. An apparatus for performing parameter difference imaging of a sample surface, said apparatus comprising:

A) a monochromatic light source for illuminating said sample surface with monochromatic light of a predetermined wavelength, B) an electronic camera for imaging and measuring said monochromatic light reflected from said sample surface, C) a means for storing at least 2 images from said electronic camera, D) a means for altering a physical parameter of said sample surface between acquisition of said images, and E) a computational means for calculating a difference between said images.

2. The apparatus of claim 1 wherein said electronic camera is a CCD camera.

3. The apparatus of claim 1 wherein said sample is selected from the group consisting of superconductors, high $T_c$ superconductors, metals, semiconductors, and insulators.

4. The apparatus of claim 1 wherein wavelength of said monochromatic light is selected such that the differential reflectance of said sample has a substantially high derivative with respect to wavelength at said wavelength of said monochromatic light.

5. The apparatus of claim 1 wherein wavelength of said monochromatic light is selected such that the differential reflectance equals zero at said wavelength of said monochromatic light.

6. The apparatus of claim 1 wherein said physical parameter is selected from the group consisting of temperature, electric field, magnetic field, exposure to light of a wavelength different than said predetermined wavelength, and mechanical stress.

7. A method of performing parameter difference imaging of a sample surface comprising the steps of:

A) illuminating said sample surface with monochromatic light of a predetermined wavelength, B) acquiring and storing a first image of said monochromatic light reflected from said sample surface with an electronic camera, C) changing a physical parameter of said sample surface, D) acquiring and storing a second image of reflected said monochromatic light with said electronic camera, and E) electronically subtracting said first image and said second image.

8. The method of claim 7 further including a normalization step comprising division of the subtracted image by an average of the first and second images.

9. The method of claim 7 wherein said sample is selected from the group consisting of superconductors, high $T_c$ superconductors, metals, semiconductors, and insulators.

10. The method of claim 7 wherein wavelength of said monochromatic light is selected such that the differential reflectance of said sample has a substantially high derivative with respect to wavelength at said wavelength of said monochromatic light.

11. The method of claim 7 wherein wavelength of said monochromatic light is selected such that the differential reflectance equals zero at said wavelength of said monochromatic light.

12. The method of claim 1 wherein said physical parameter is selected from the group consisting of temperature, electric field, magnetic field, exposure to light of a wavelength different than said predetermined wavelength, and mechanical stress.

* * * * *

UNITED STATES PATENT AND TRADEMARK OFFICE
CERTIFICATE OF CORRECTION

PATENT NO.    : 5,946,102
DATED         : August 31, 1999
INVENTOR(S)   : Matthew J. Holcomb It is certified that error appears in the above-identified patent and that said Letters Patent is hereby corrected as shown below:

Column 1,
Line 40, "Mumolas" should read -- Mumola's --.
Line 52, "Kimuras" should read -- Kimura's --.
Line 67, "Scheitingers" should read -- Scheitinger's --.

Column 2,
Line 67, "Scheitingers" should read -- Scheitinger's --.

Figure 11A:
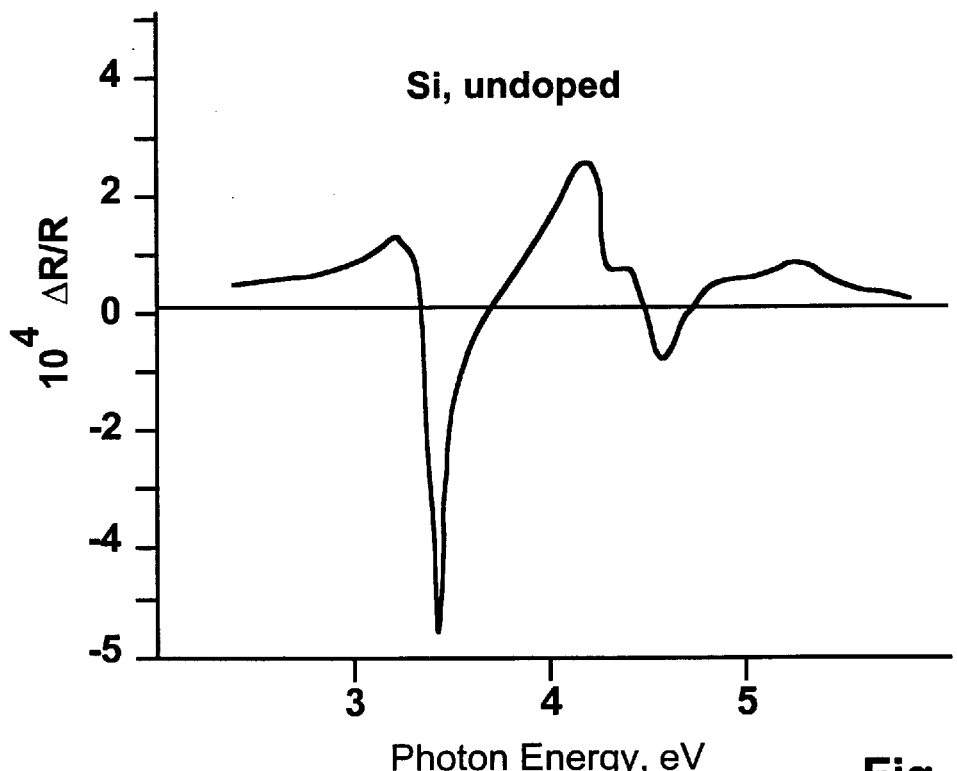
FIG. 11 is a set of graphs of the TD spectra for several samples of silicon with different levels and types of doping.
Figure 11B:
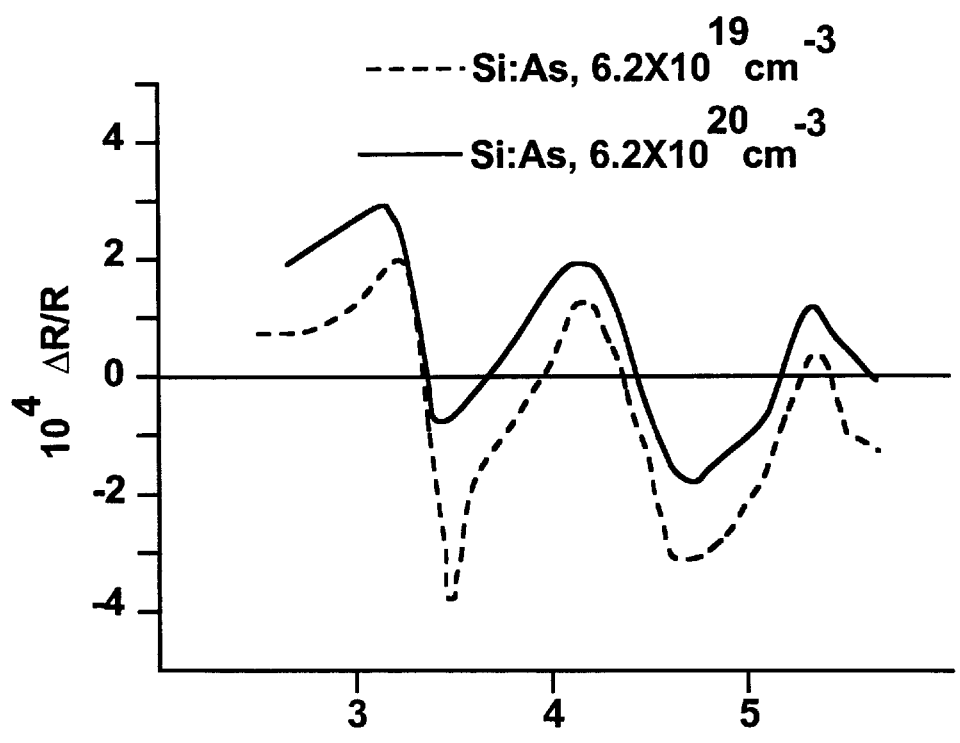

Column 4,
Line 1, "FIG. 11" should read -- FIGS. 11A-B --.
Line 3, "FIG. 12" should read -- FIGS. 12A-B --.

Column 5,
Line 21, "of" should read -- by --.

Column 6,
Line 43, "materials" should read -- material's --.

Column 8,
Line 32, "art Photo-reflectance Spectroscopy" should read -- art of Photo-reflectance Spectroscopy --.
Line 33, "use Photo-difference imaging" should read -- use a Photo-difference imaging --.
Line 65, "materials" should read -- material's --.

Column 10,
Lines 59 and 64, "wherein wavelength of said" should read -- wherein said wavelength of said --.

Column 11,
Line 15, "of reflected said" should read -- of said reflected --.

UNITED STATES PATENT AND TRADEMARK OFFICE
CERTIFICATE OF CORRECTION

PATENT NO.   : 5,946,102
DATED        : August 31, 1999
INVENTOR(S)  : Matthew J. Holcomb It is certified that error appears in the above-identified patent and that said Letters Patent is hereby corrected as shown below:

Column 12,
Lines 4 and 10, "wherein wavelength of said" should read -- wherein said wavelength of said --.
Line 15, "1" should read -- 7 --.

Signed and Sealed this

Eleventh Day of May, 2004

JON W. DUDAS
*Acting Director of the United States Patent and Trademark Office*